United States Patent
Cousins et al.

(10) Patent No.: US 10,336,750 B2
(45) Date of Patent: Jul. 2, 2019

(54) COMPOSITION AND METHODS FOR THE TREATMENT OF CAMKK2-MEDIATED DISORDERS

(71) Applicant: Duke University, Durham, NC (US)

(72) Inventors: Scott W. Cousins, Durham, NC (US); David M. Gooden, Durham, NC (US); Priyatham S. Mettu, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 15/847,998

(22) Filed: Dec. 20, 2017

(65) Prior Publication Data

US 2018/0118743 A1 May 3, 2018

Related U.S. Application Data

(63) Continuation of application No. 15/016,623, filed on Feb. 5, 2016, now Pat. No. 9,879,005.

(60) Provisional application No. 62/112,369, filed on Feb. 5, 2015.

(51) Int. Cl.
*C07D 471/04* (2006.01)
*C07D 471/06* (2006.01)

(52) U.S. Cl.
CPC ......... *C07D 471/04* (2013.01); *C07D 471/06* (2013.01)

(58) Field of Classification Search
CPC .............................. C07D 471/04; C07D 471/06
See application file for complete search history.

(56) References Cited

U.S. PATENT DOCUMENTS 8,207,185 B2 * 6/2012 Means ............... A61K 31/4745
514/265.1

FOREIGN PATENT DOCUMENTS

WO 2008045273 A2 4/2008
WO 2012024255 A2 2/2012

OTHER PUBLICATIONS

Anderson, Kristin A. et al., "Hypothalamic CaMKK2 Contributes to the Regulation of Energy Balance" Cell Metabolism, vol. 7, pp. 377-388, May 2008.
Espinosa-Heidmann, Diego G. et al., "Bone Marrow Transplantation Transfers Age-Related Susceptibility to Neovascular Remodeling in Murine Laser-Induced Choroidal Neovascularization" The Association for Research in Vision and Ophthalmology, Inc. vol. 54, No. 12, pp. 7439-7449, Nov. 2013.
Racioppi, Luigi et al., "Calcium/Calmodulin-dependent Protein Kinase Kinase 2 Regulates Macrophage-mediated Inflammatory Responses" The Journal of Biological Chemistry vol. 287, No. 14, pp. 11579-11591, Mar. 30, 2012.

(Continued)

*Primary Examiner* — San Ming R Hui
(74) *Attorney, Agent, or Firm* — Olive Law Group, PLLC; Nathan P. Letts

(57) ABSTRACT

The present disclosure provides compositions and methods for treating ocular disorders in mammals especially in and not limited to humans and mice. The present disclosure further provides methods of treating cancer and appetite suppression using the compositions which are novel small molecule inhibitors of CaMKK2. In addition, these derived compositions can regulate non-ocular disorders, such as cancer and appetite suppression by modulating and inhibiting CaMKK2 and the regulation of the macrophage mediated diseases.

14 Claims, 9 Drawing Sheets

(56) References Cited

OTHER PUBLICATIONS

Tokumitsu, Hiroshi et al., "STO-609, a Specific Inhibitor of the Ca2/Calmodulin-dependent Protein Kinase Kinase" The Journal of Biological Chemistry, vol. 277, No. 18, Issue of May 3, pp. 15813-15818, 2002.

* cited by examiner

Capillary Pattern
*Responsive to anti-VEGF*

Human ICG

Mouse Laser CNV
Lectin-stained

Branching Arteriolar Pattern (NVR)
*Resistant to anti-VEGF*

Human ICG

Mouse Laser CNV
Lectin-stained

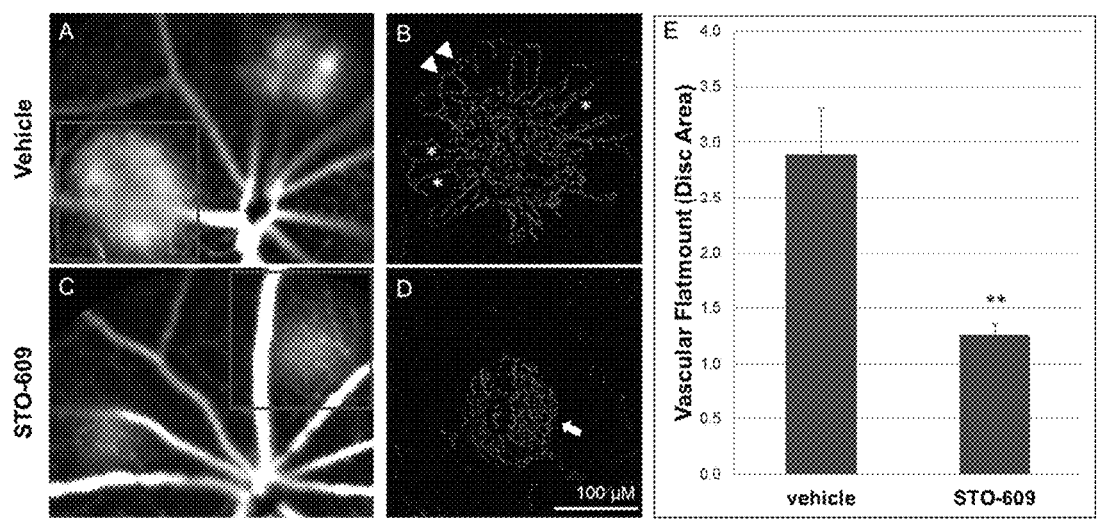
Figure 7. Ocular Application of CaMKK2 Inhibitor Drug (STO-609)

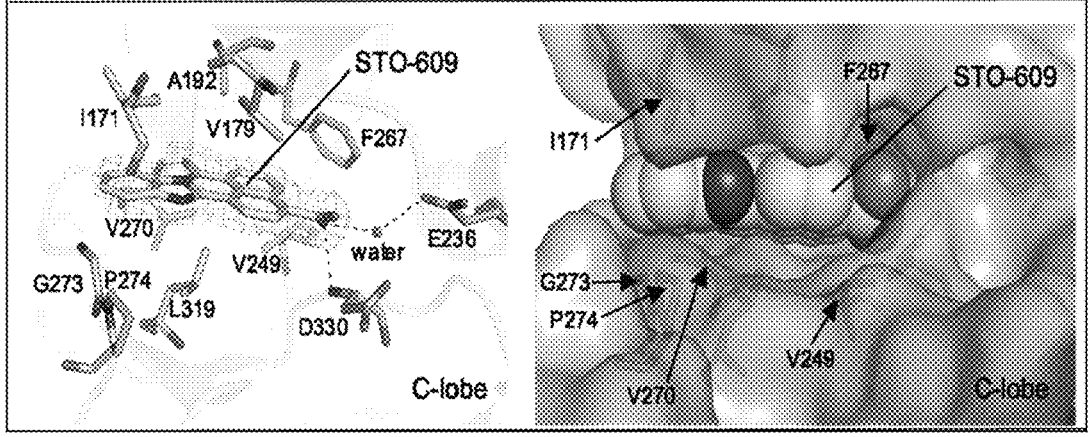

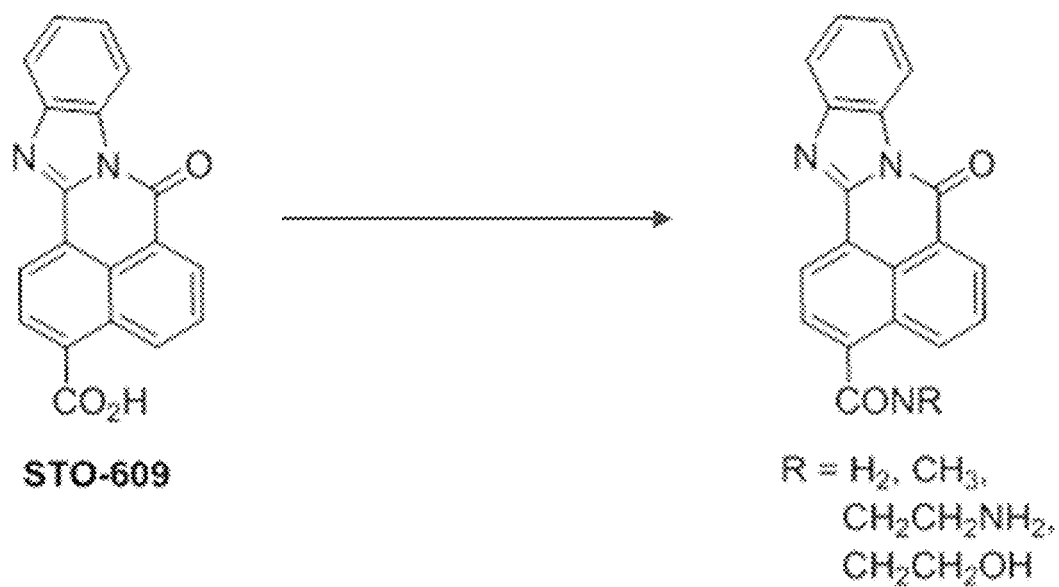
Fig. 9. Synthetic Strategy for Analogs

COMPOSITION AND METHODS FOR THE TREATMENT OF CAMKK2-MEDIATED DISORDERS

CROSS REFERENCE TO RELATED APPLICATIONS

This application is a continuation of U.S. Ser. No. 15/016,623, filed Feb. 5, 2016, which claims the benefit of 62/112,369 filed Feb. 5, 2015, Cousins et al., which is hereby incorporated by reference in its entirety.

1. FIELD

The present disclosure provides compounds and methods for the treatment of Calcium/Calmodulin-dependent Kinase Kinase 2 (CaMKK2)-mediated disorders.

2. BACKGROUND

2.1. Introduction

Age-related macular degeneration (AMD) includes neovascular age-related macular degeneration (NVAMD), defined by pathological choroidal new vessels (CNV) under the macula. Neovascular age-related macular degeneration (NVAMD), defined by pathological choroidal new vessels (CNV) under the macula, is the leading cause of vision loss in in the elderly (see e.g., Congdon N, et al. (2004) *Archives of ophthalmology;* 122: 477-485; Green W R, Mol Vis 1999; 5:27).

NVAMD patients showed improved vision outcomes after intraocular injections of anti-vascular endothelial growth factor (VEGF). However, around 50% of treated patients manifest persistent plasma leakage, blood, lesion growth or progressive fibrosis, collectively called persistent disease activity (PDA) (Brown D M et al. (2006) *The New England journal of medicine* 355: 1432-1444; Heiser J S et al. (2012) *Ophthalmology; Epub* 2012/10/23; Rosenfield P J et al. (2006) *The New England journal of medicine* 355: 1419-1431; Martin D F et al. (2012) *Ophthalmology* 119: 1388-1398; Martin D F et al. (2011) *The New England journal of medicine* 364: 1897-1908). There are no treatments existing for PDA. Therefore, these patients are at risk for long-term vision loss (Rosenfeld P J et al. (2011) *Ophthalmology* 118: 523-530; Ying G-S et al. (2012) *Invest Ophthalmol Vis Sci* 53: 3681).

PDA occurs most frequently in NVAMD lesions with arteriolarization and perivascular fibrosis, a distinct pathology known as neovascular remodeling (NVR). Histopathology in surgically excised CNV of NVAMD patients demonstrate increased frequency of macrophages in association with NVR lesions (Tatar O et al. (2009) *The British journal of ophthalmology* 93: 159-165). In addition, systemic depletion of macrophages abrogates the NVR phenotype in mice resulting in smaller lesions (presumed capillaries) with less fibrosis (Espinosa-Heidmann D G et al. (2003) *Invest Ophthalmol Vis Sci* 44: 3586-3592). Thus, macrophages appear to promote NVR, and therapies directed against macrophages may be effective for the treatment of NVR in affected patients.

The intermediate kinase Calcium/Calmodulin-dependent Kinase Kinase 2 (CaMKK2) is a key regulatory kinase that has been shown to amplify macrophage effector function (Racioppi L et al. (2012) J Biol Chem 287: 11579-11591). CaMKK2 is activated within tumor-associated macrophages, and knockout of CaMKK2 attenuates macrophage-mediated tumor vascularization and growth. However, consistent with CaMKK2's role as an amplifier of effector function, mice null for CaMKK2 do not develop immunosuppression or susceptibility to infections. Thus, CaMKK2 appears to be a promising target for macrophage-mediated inflammation, including macrophage-mediated NVR in the setting of NVAMD and macrophage-mediated tumor growth in the setting of cancer.

In addition to this role in macrophage function, CaMKK2 is also expressed in areas of the brain that regulate satiety. As a result, there has been interest in identifying inhibitors of CaMKK2 (that cross the blood-brain barrier) as appetite-control drugs.

3. SUMMARY OF THE DISCLOSURE

The present disclosure provides, in part, novel compounds that are small molecule inhibitors of the regulatory kinase Calcium/Calmodulin-dependent Kinase Kinase 2 (CaMKK2), and methods of using said compounds for the treatment of appetite suppression, cancer, and ocular diseases, including both front-of-the-eye (i.e. corneal/conjunctival disorders) and back-of-the-eye (i.e. retinal and choroidal disorders) indications. Back-of-the-eye indications include, but are not limited to, age-related macular degeneration, diabetic retinopathy, retinal vein occlusion, and glaucoma.

One aspect of the present disclosure provides a compound comprising, consisting of, or consisting essentially of the general formula (I):

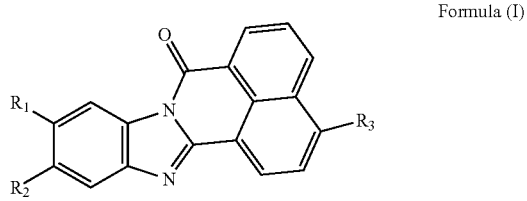

Formula (I)

or a pharmaceutically acceptable salt, solvate, hydrate, prodrug or derivative thereof, wherein $R_1$ and $R_2$ are Hydrogen (H), then $R_3$ is selected from the group consisting of

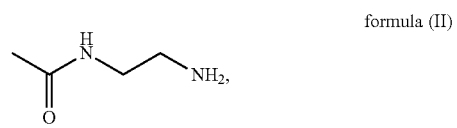

formula (II)

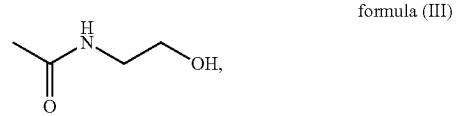

formula (III)

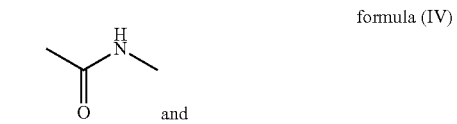

formula (IV)

and formula (V)

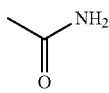

Another aspect of the present disclosure provides a compound comprising, consisting of, or consisting essentially of the general formula (I)

Formula (I)

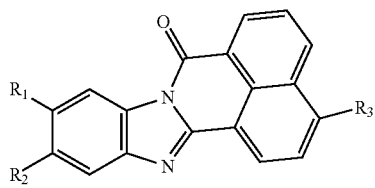

or a pharmaceutically acceptable salt, solvate, hydrate, prodrug or derivative thereof, wherein $R_3$ comprises a carboxylic acid ($CO_2H$) and $R_1$ and $R_2$ are selected from the group consisting of:

formula (VI)

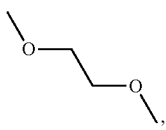

formula (VII)

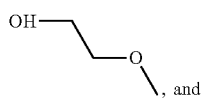
, and formula (VIII)

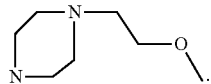
.

Another aspect of the present disclosure provides a compound comprising, consisting of, or consisting essentially of the chemical formula:

Formula (IX)

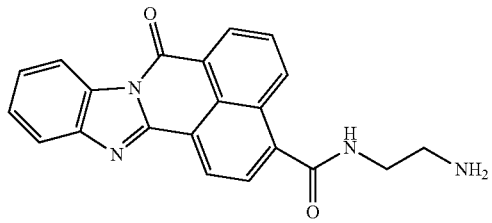

or a pharmaceutically acceptable salt, solvate, hydrate, prodrug or derivative thereof.

Another aspect of the present disclosure provides a compound comprising, consisting of, or consisting essentially of the chemical formula:

Formula (X)

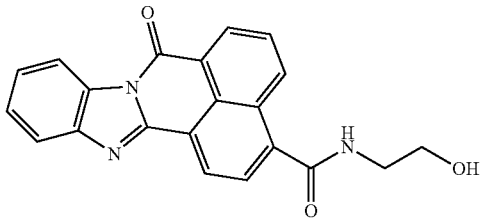

or a pharmaceutically acceptable salt, solvate, hydrate, prodrug or derivative thereof.

Another aspect of the present disclosure provides a compound comprising, consisting of, or consisting essentially of the chemical formula:

Formula (XI)

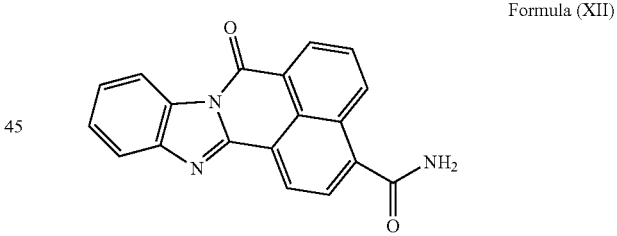

or a pharmaceutically acceptable salt, solvate, hydrate, prodrug or derivative thereof.

Another aspect of the present disclosure provides a compound comprising, consisting of, or consisting essentially of the chemical formula:

Formula (XII)

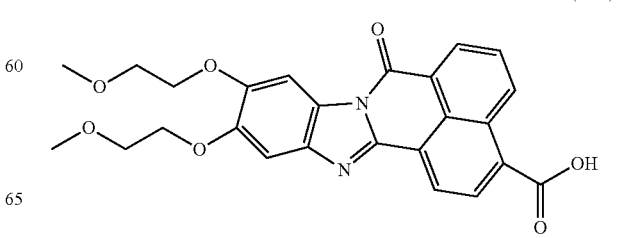

or a pharmaceutically acceptable salt, solvate, hydrate, prodrug or derivative thereof.

Another aspect of the present disclosure provides a compound comprising, consisting of, or consisting essentially of the chemical formula:

Formula (XIII)

or a pharmaceutically acceptable salt, solvate, hydrate, prodrug or derivative thereof.

Another aspect of the present disclosure provides a compound comprising, consisting of, or consisting essentially of the chemical formula:

Formula (XIV)

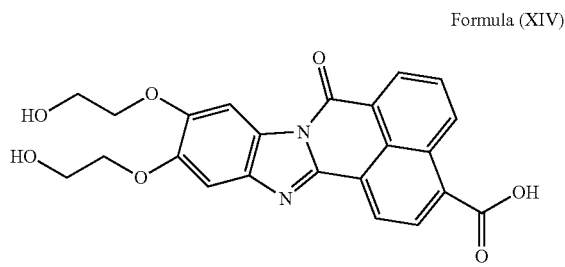 [SMILES: O=C(O)c1ccc2c3c1cccc3c(=O)n1c3cc(OCCO)c(OCCO)cc3nc21]

or a pharmaceutically acceptable salt, solvate, hydrate, prodrug or derivative thereof.

Another aspect of the present disclosure provides a compound comprising, consisting of, or consisting essentially of the chemical formula:

Formula (XV)

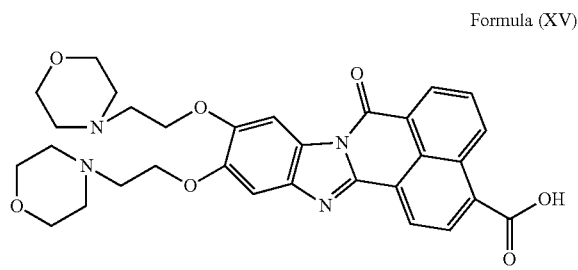 [SMILES: O=C(O)c1ccc2c3c1cccc3c(=O)n1c3cc(OCCN4CCOCC4)c(OCCN4CCOCC4)cc3nc21]

or a pharmaceutically acceptable salt, solvate, hydrate, prodrug or derivative thereof.

Another aspect of the present disclosure provides a pharmaceutical composition comprising, consisting of, or consisting essentially of a compound as described herein and a pharmaceutically acceptable carrier.

Yet another aspect of the present disclosure provides a method of modulating CaMKK2 activity in a cell comprising, consisting of, or consisting essentially of administering to the cell an effective amount of a compound as provided herein such that the CaMKK2 activity is modulated.

Another aspect of the present disclosure provides a method of inhibiting CaMKK2 activity in a target cell comprising, consisting of, or consisting essentially of administering to the cell an effective amount of a compound as described herein such that the CaMKK2 activity is inhibited.

Another aspect of the present disclosure provides a method for treating an ocular indication in a subject comprising, consisting of, or consisting essentially of administering to the subject an effective amount of a compound as described herein such that the ocular indication is treated. In some embodiments, the ocular indication comprises age-related macular degeneration (AMD), including neovascular AMD and neovascular AMD with persistent disease activity (PDA) in spite of anti-VEGF therapy. In other embodiments, the ocular indication comprises other ocular diseases characterized by macrophage-mediated inflammation, including but not limited to allergic conjunctivitis, dry eye disease, diabetic retinopathy, retinal vein occlusion, and glaucoma.

Another aspect of the present disclosure provides a method for treating cancer in a subject comprising, consisting of, or consisting essentially of administering to the subject an effective amount of a compound as described herein such that the cancer is treated. In some embodiments, the cancer is characterized by CaMKK2 activity.

Yet another aspect of the present disclosure provides a method for treating a subject with a satiety-control disorder comprising, consisting of, or consisting essentially of administering to the subject an effective amount of a compound as described herein such that the satiety-control disorder is treated.

Another aspect of the present disclosure provides all that is described and illustrated herein.

4. BRIEF DESCRIPTION OF THE FIGURES

FIG. 1 depicts the distinct biologies of neovascularization, capillary maturation and neovascular remodeling (NVR), the latter of which is an important cause of persistent disease activity (PDA) in spite of anti-VEGF therapy in neovascular age-related macular degeneration (NVAMD). In NVR, blood-derived macrophages release fibrogenic growth factors that recruit and activate vascular smooth muscle cells and myofibroblasts, transforming the nascent capillary lesion into large-caliber branching arterioles with perivascular fibrosis.

FIG. 2 demonstrates capillary morphology of choroidal neovascularization (CNV) by ICG in human with NVAMD (left image) and by lectin flatmount in experimental model of laser-induced CNV in mice (right image). Capillary development occurs with angiogenesis and maturation, and patients with this CNV morphology are responsive to anti-VEGF therapy.

FIG. 3 demonstrates branching arteriolar morphology of CNV, which is apparent by ICG in human with NVAMD (left image) and by lectin flatmount in experimental model of laser-induced CNV in mice (right image). Branching arteriolar morphology reflects neovascular remodeling (NVR), and patients who manifest this distinct pathobiology manifest persistent disease activity (PDA) in spite of anti-VEGF therapy.

Figure 6:
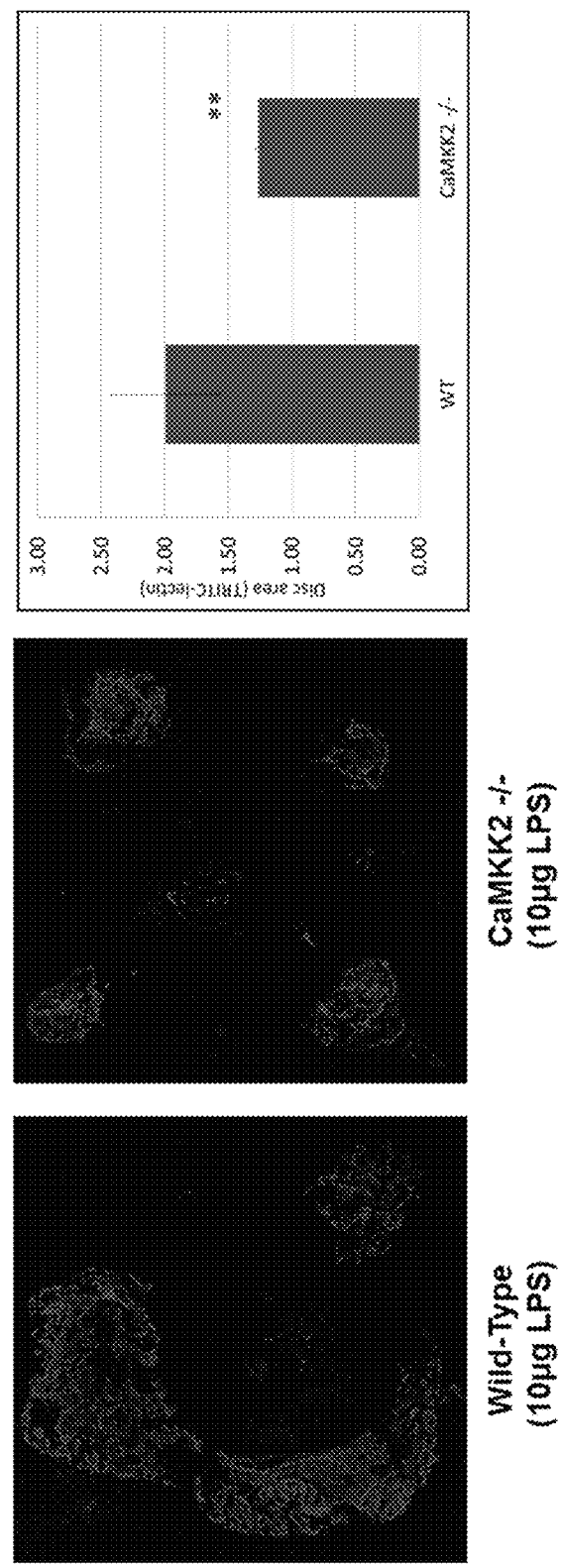

FIG. 6 demonstrates diminished NVR in mice null for expression of CaMKK2, as compared to wild-type mice, in the model of experimental laser-induced CNV following monocyte activation with systemic low-dose lipopolysaccharide (LPS).

FIG. 7 demonstrates inhibition of NVR by local ocular application of STO-609, a small molecule inhibitor of CaMKK2, in the aging model of NVR in experimental laser-induced CNV.

FIG. 8 shows the crystal structure of the STO-609 CaMKK2 complex.

FIG. 9 shows the synthetic scheme to prepare the compounds of the disclosure.

5. DETAILED DESCRIPTION OF THE DISCLOSURE

For the purposes of promoting an understanding of the principles of the present −++disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The present disclosure is based, in part, on the discovery of Calcium/Calmodulin Kinase Kinase 2 (CaMKK2) as a target for treatment of ocular indications, such as age-related macular degeneration (AMD).

Calcium/calmodulin-dependent protein kinase kinase 2 (CaMKK2) is an enzyme encoded by the CAMKK2 gene (see, e.g., Hsu L S. et al. (1998) *J Biomed Sci* 5 (2): 141-9). CaMKK2 was first proposed to be a key mediator of central nervous system appetite control in 2008, as it was shown to be present in centers of the brain controlling satiety. More recently, CaMKK2 has been shown to be an important regulatory kinase in macrophages, and consequently has important effects on macrophage-mediated biology in cancer and inflammation.

CaMKK2 belongs to Serine/Threonine protein kinase family, and to the $Ca^{2+}$/calmodulin-dependent protein kinase subfamily (Hsu L S, et al. (1998) *J Biomed Sci* 5 (2): 141-9). This protein is regulated by cytoplasmic calmodulin levels and inflammatory stimuli. CaMKK2 phosphorylates calcium/calmodulin-dependent kinase I and IV (CaMKI and CaMKIV) and adenosine monophosphate-activated protein kinase (AMPK), which regulate numerous macrophage functions (Hsu L et al. (2001) *J. Biol. Chem.* 276 (33): 31113-23). Activation of these kinases and downstream signaling pathways promote macrophage activation and subsequent inflammation. Thus, CaMKK2 has emerged as a promising therapeutic target for macrophage-mediated diseases, including age-related macular degeneration and cancers.

Furthermore, CaMKK2 also activates protein tyrosine kinase 2 beta (PTK2B). This pathway mediates many proinflammatory and fibrogenic effector systems.

Whole-body knockout of CaMKK2 in mice impairs the ability of macrophages to adhere and extend membrane processes, prevents macrophage accumulation and inhibits cytokine release in response to low-dose lipopolysaccharide (LPS) (Racioppi L et al. (2012) *The journal of biological chemistry* 287: 11579-11591).

Given the hypothesis that CaMKK2 inhibition may be effective for the treatment of multiple disorders, including appetite disorders, cancer, and diseases of the eye, it was hypothesized that the small molecule STO-609, which has well characterized as a specific inhibitor of CaMKK2, would provide a promising starting point from which novel CaMKK2 modulators could be created. Like many kinase inhibitors, STO-609 suffers from relative insolubility making it a poor candidate for oral dosing. However, with knowledge of the biochemical structure of STO-609, the inventors were able to design a formulation for local ocular (i.e. periocular and topical) application. Additionally, with knowledge of how STO-609 orients in the ATO binding pocket of CaMKK2, the inventors were able to determine which regions of STO-609 are best suited for the addition of solubilizing groups to the molecular framework. That region revealed at least two regions amenable to chemical modification. The first region to modify was the carboxylic acid of STO-609.

Another aspect of present invention is pharmaceutical composition of compounds with formula of the preceding aspects or a pharmaceutically acceptable salt, solvate, hydrate, or derivative thereof.

The term "administering" is defined as to describe the dosage of a compound or composition, means a single does or multiple doses of the compounds or compositions. Administering is not limited to the method of giving the doses of compounds or compositions.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-l-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical —OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with a halogen(s) such as difluoro or trifluoro. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen, such as fluorine.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted.

In certain embodiments, the cycloalkyl group can be $C_{3-10}$ cycloalkyl, such as, for example, $C_6$ cycloalkyl.

"Disease" refers to any disease, disorder, condition, symptom, or indication.

The term "effective amount" or "therapeutically effective amount" are used interchangeably and it means an amount sufficient to effect beneficial or desirable biological and/or clinical results.

"Halogen" refers to a fluoro, chloro, bromo, or iodo group.

The term "modulating" refers to the ability of a compound to increase or decrease the function and/or expression of CaMKK2, where CaMKK2 function may include kinase activity and/or macrophage mediated process. Modulation may occur in vitro or in vivo. Modulation, as described herein, includes the inhibition or activation of CaMKK2 function and/or the down regulation or up regulation of CaMKK2 expression, either directly or indirectly. A modulator preferably activates CaMKK2 function and/or up regulates CaMKK2 expression. More preferably, a modulator activates or inhibits CaMKK2 function and/or up regulates or down regulates CaMKK2 expression. Most preferably, a modulator inhibits CaMKK2 function and/or down regulates CaMKK2 expression. The ability of a compound to inhibit CaMKK2 function can be demonstrated in an neovascular remodeling (NVR) in wet AMD (e.g., laser CNV model).

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Prodrug" refers to a precursor or derivative form of a pharmaceutically active substance that is less bioactive compared to the parent drug and is capable of being enzymatically activated or converted into the more active parent form. Prodrug forms of the compounds described herein may designed to improve bioavailability or stability or reduce toxicity. For example, compounds of the invention having free amino, amido, carboxylic, hydroxyl, or thiol groups can be converted into prodrugs. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Prodrugs may also include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes beta-alanine, citrulline, demosine, gamma-aminobutyric acid, homocysteine, homoserine, 4-hydroxyproline, hydroxylysine, isodemosine, 3-methylhistidine, norvalin, methionine sulfone, and ornithine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

The term "subject" is defined herein to include animals such as mammals, including, but not limited to, primates (e.g., humans), cows, sheep, goats, horses, dogs, cats, rabbits, rats, mice and the like.

"Substituted" refers to a group in which one or more hydrogen atoms are each independently replaced with the same or different substituent(s). Typical substituents include, but are not limited to, $CO_2H$, cyano, difluoro, halogen, hydroxyl, $-N_3$, $-NH_2$, $-SO_{(1-3)}H$, $-SH$, or trifluoro.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

One aspect of the present disclosure provides a method of modulating CaMKK2 in a subject comprising, consisting of, or consisting essentially of administering to the subject an effective amount of any of the compound as described from claims 1-10 herein.

The term "inhibiting" refers to preventing, reducing and halting progression of certain chemical or physical mechanism within the subject.

One aspect of the present disclosure provides a method of inhibiting CaMKK2 in a subject comprising, consisting of, or consisting essentially of administering to the subject an effective amount of any of the compound as described from claims 1-10 herein.

The term "treating" as used herein refers to any type of treatment that imparts a benefit to a patient afflicted with a disease, including improvement in the condition of the patient (e.g., in one or more symptoms), prevent the development of disease, delay the onset of the disease, etc.

The term "age-related macular degeneration" (AMD) refers to a progressive eye condition affecting the macula of the eye, where a small spot near the center of the retina and the part of the eye needed for sharp, central vision, which allow the subjects to see straight.

The term "cancer" refers to diseases in which abnormal cells divide without control and are able to invade other parts of body such as tissues and organs.

The term "frontal and distal eye indication" refers to any symptom that suggests certain medical treatment is necessary for front and back of the eye.

The term "appetite suppression" refers to control or decrease of the appetite in the subject.

One aspect of the present disclosure provides a method of treating appetite suppression in a subject comprising, consisting of, or consisting essentially of administering to the subject a therapeutically effective amount of any of the compound as described from claim 1-10 or 11-12 herein.

5.1. Definitions

The While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within±25% of 40 (e.g., from 30 to 50), within±20%, ±15%, ±10%, ±9%, ±8%, ±7%, ±6%, ±5%, ±4%, ±3%, ±2%, ±1%, less than±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, ***.

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Experimental Mouse Models of NVR That Have Demonstrated That Blood-derived Macrophages Regulate NVR Neovascular age-related macular degeneration (NVAMD), which is defined by growth of pathological choroidal new vessels (CNV) under the macula, remains the leading cause of vision loss in the elderly. (see e.g., Congdon N, et al. (2004) *Archives of ophthalmology;* 122: 477-485; Green W R, Mol Vis 1999; 5:27). Many NVAMD patients who are treated with anti-vascular endothelial growth factor (VEGF) therapies have improved vision. However, around 50% of patients demonstrate persistent disease activity (PDA) in spite of therapy (Brown D M et al. (2006) *The New England journal of medicine* 355: 1432-1444; Heiser J S et al. (2012) *Ophthalmology;* Rosenfield P J et al. (2006) *The New England journal of medicine* 355: 1419-1431; Martin D F et al. (2012) *Ophthalmology* 119:1388-1398; Martin D F et al. (2011) *The New England journal of medicine* 364: 1897-1908.).

Figure 1:
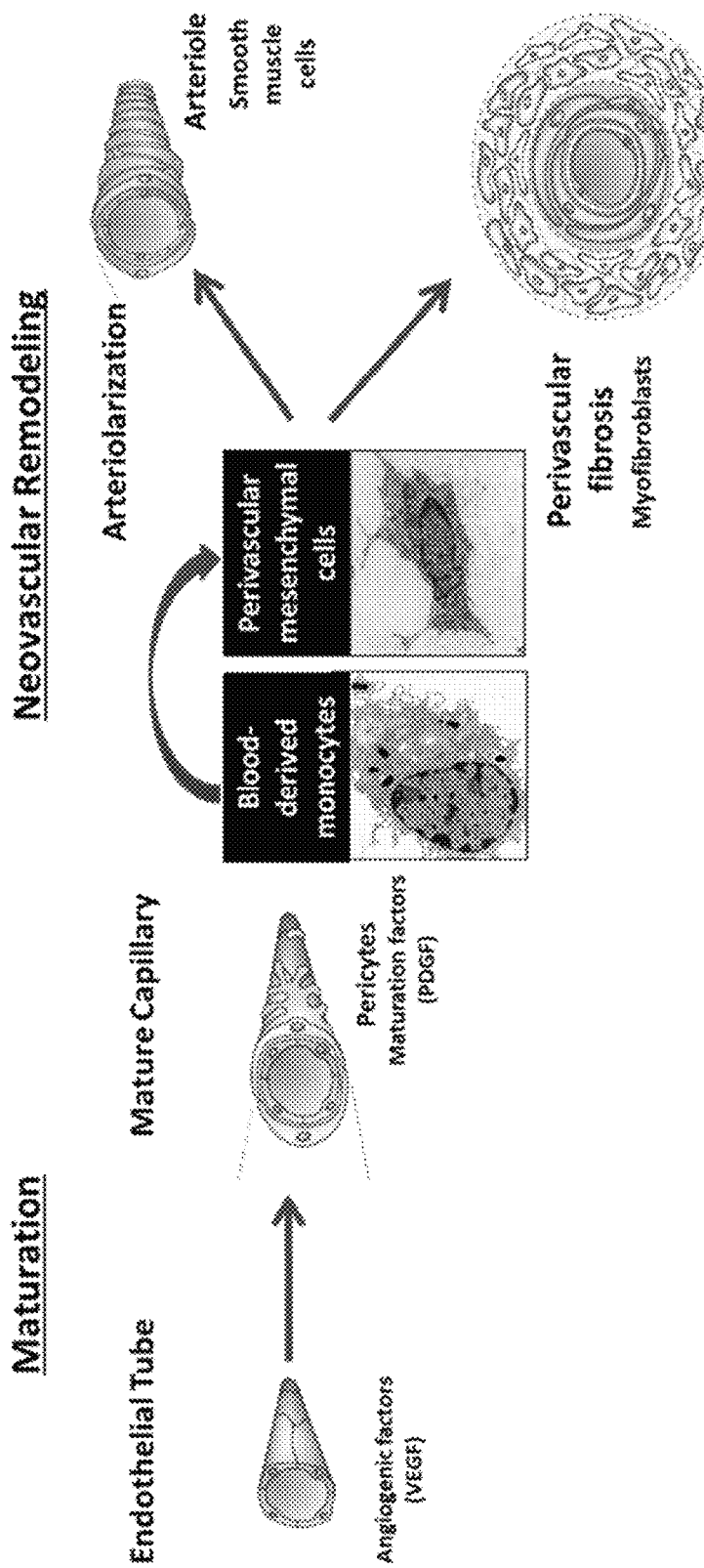

A major cause of PDA is NVR, the transformation of capillary new vessels into branching arterioles with perivascular fibrosis early in neovessel development. In experimental laser-induced CNV models in mice, it has been shown that blood-derived macrophages regulate NVR development by production of fibrogenic growth factors such as TGF-β and CTGF, which function to recruit and differentiate vascular smooth muscle cells and myofibroblasts. (see FIG. 1).

Figure 2:
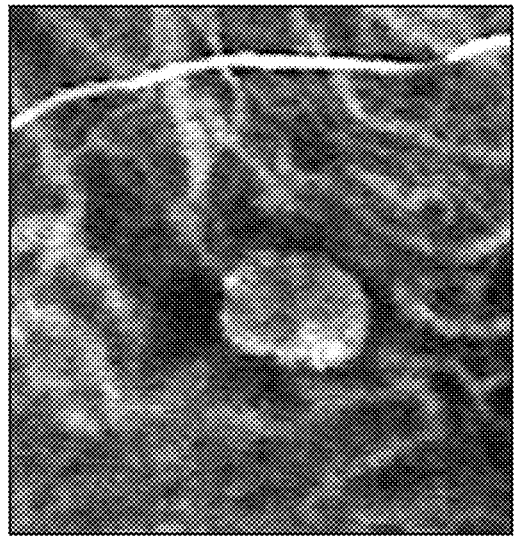
Figure 2:
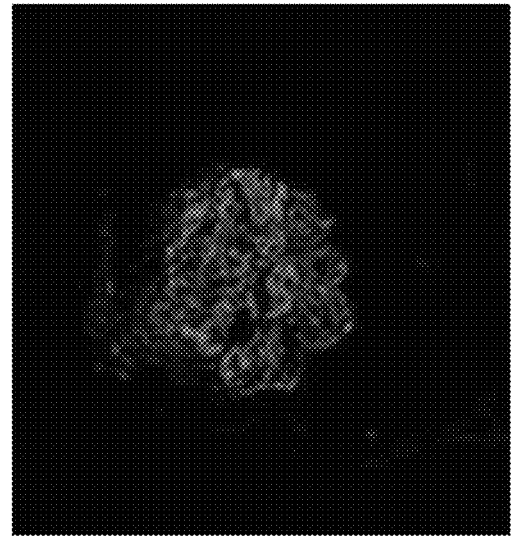

FIG. 2 demonstrates capillary morphology of choroidal neovascularization (CNV) by indocyanine green angiography (ICG) in human with NVAMD (left image) and by lectin flatmount in experimental model of laser-induced CNV in mice (right image). Capillary development occurs with angiogenesis and maturation, and patients with this CNV morphology are responsive to anti-VEGF therapy. The inventors have developed ICG, which depicts CNV morphology, as an imaging biomarker for response to anti-VEGF therapy. PDA occurs rarely in eyes with capillary pattern (less than 10% of PDA cases).

Figure 3:
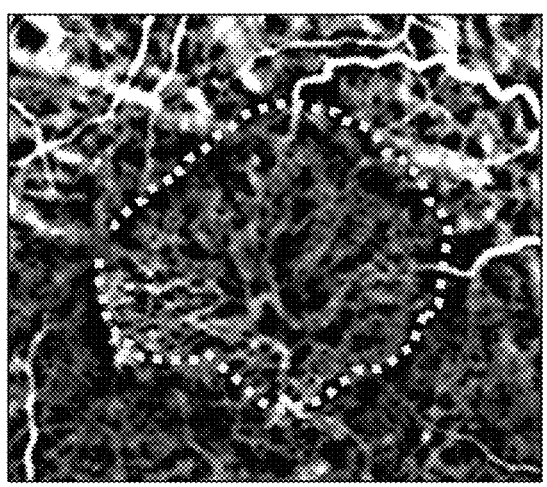
Figure 3:
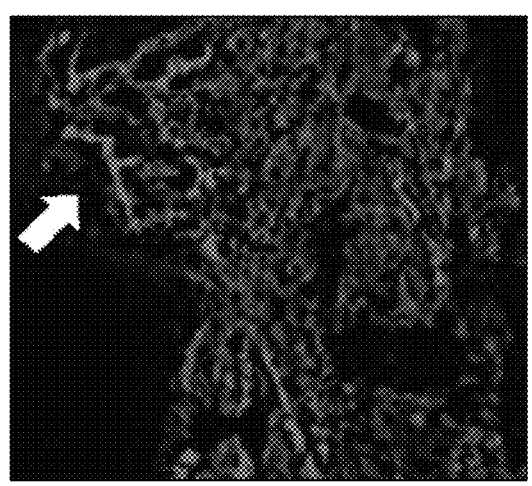

FIG. 3 demonstrates Branching arteriolar morphology of choroidal neovascularization (CNV) by indocyanine green angiography (ICG) in human with NVAMD (left image) and by lectin flatmount in experimental model of laser-induced CNV in mice (right image). Following capillary formation, development of Branching arteriolar morphology occurs following activation and recruitment of vascular smooth muscle cells and myofibroblasts, a process known as neovascular remodeling (NVR). Patients with this CNV morphology are resistant to anti-VEGF therapy, manifesting persistent disease activity in spite of treatment (representing over 60% of PDA cases. The histopathology of NVR lesions both in the mouse and in the surgically excised CNV of NVAMD patients demonstrated a high frequency of associated macrophages, which is not present in capillary lesions (Tatar O et al. (2009) *The British journal of ophthalmology* 93: 159-165.).

Figure 4:
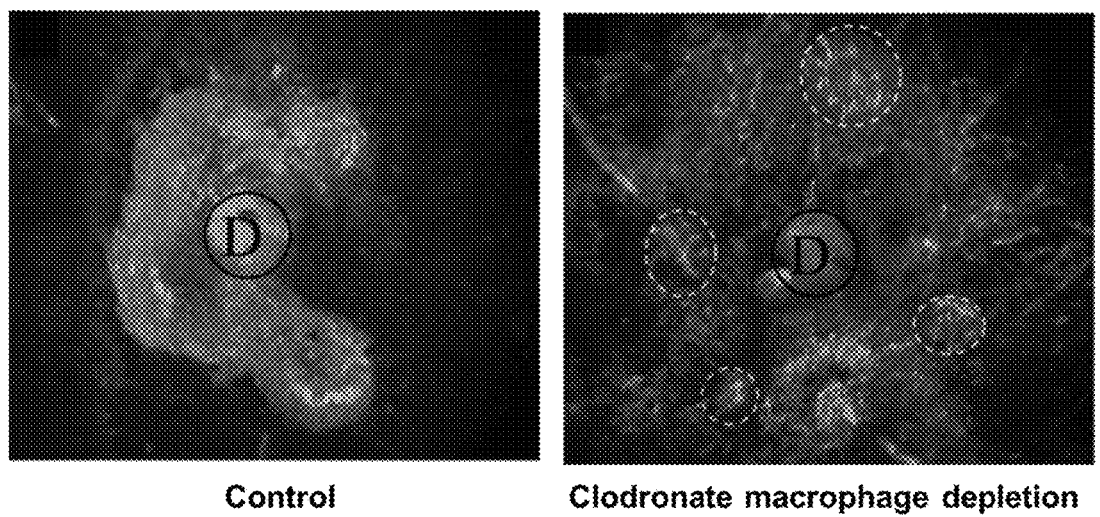
FIG. 4 depicts choroidal flatmounts by FITC-dextran in the aging model of NVR in experimental laser-induced CNV. Whereas sham control-treated aged (16 month-old) mice developed confluent CNV lesions with arterioles and perivascular fibrosis, mice subjected to systemic depletion of macrophages with clodronate had abrogation of the NVR phenotype, resulting in smaller lesions with less fibrosis.

FIG. 4 depicts choroidal flatmounts by FITC-dextran in the aging model of NVR in experimental laser-induced CNV. Whereas sham control-treated aged (16 month-old) mice developed confluent CNV lesions with arterioles and perivascular fibrosis, mice subjected to systemic depletion of macrophages with clodronate had abrogation of the NVR phenotype, resulting in smaller lesions with less fibrosis. This data support the concept that macrophages promote NVR in NVAMD and provide a clear rationale for novel therapeutics directed against activated macrophages for the treatment of PDA in NVAMD (Espinosa-Heidmann D G et al. (2003) *Invest Ophthalmol Vis Sci* 44: 3586-3592.).

Figure 5:
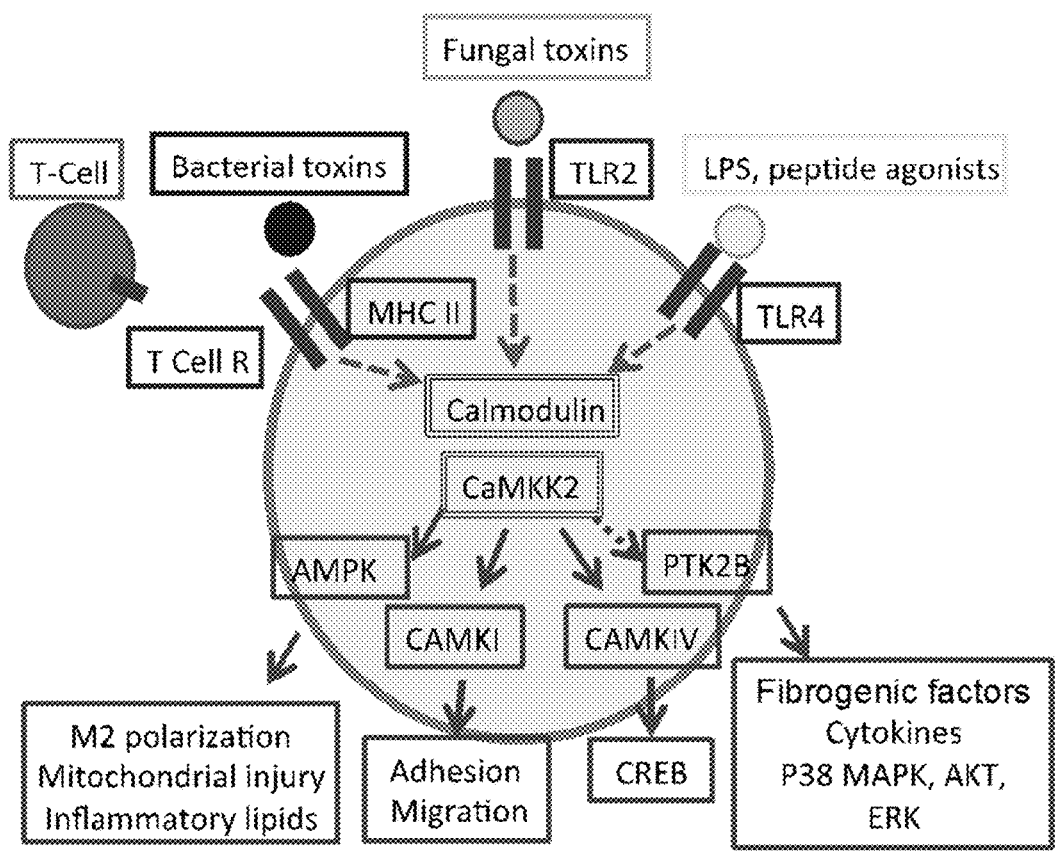
FIG. 5 depicts activation of downstream kinases by CaMKK2, and how subsequent activation of these pathways (CaMKI, CaMKIV, AMPK, PTK2B), mediate many critical functions in macrophages, including many proinflammatory and fibrogenic effector systems.

FIG. 5 depicts activation of downstream kinases by CaMKK2, and how subsequent activation of these pathways (CaMKI, CaMKIV, AMPK, PTK2B), mediate many critical functions in macrophages, including many proinflammatory and fibrogenic effector systems. Following exposure to "nonclassical" activating stimuli, including pathogen-associated toxins like lipopolysaccharides, exotoxins and cell wall toxins, CaMKK2 activity is increased, as it is regulated by cytoplasmic calcium levels and activated calmodulin-.CaMKK2 directly phosphorylates three substrates calcium/calmodulin-dependent protein kinases I (CaMKI) and IV (CaMKIV) and adenosine monophosphate-activated protein kinase (AMPK), and activates protein tyrosine kinase 2B (PTK2B), all of which regulate macrophage functions, especially many proinflammatory and fibrogenic effector systems. Macrophages derived from CaMKK2 knockout mice had diminished ability to adhere and extend membrane processes. Additionally, macrophage accumulation is prevented and cytokine release in response to lipopolysaccharides (LPS) is inhibited. (Racioppi L et al. (2012) *The journal of biological chemistry* 287: 11579-11591.)

FIG. 6 demonstrates diminished NVR in mice null for expression of CaMKK2, as compared to wild-type (WT) mice, in the model of experimental laser-induced CNV following monocyte activation with systemic low-dose lipopolysaccharide (LPS).Whereas LPS-exposed WT mice demonstrate large branching arterioles and terminal vascular loops (hallmark features of NVR), LPS-exposed CaMKK2 knockout mice have capillary-predominant lesions that are smaller in size.

FIG. 7 demonstrates inhibition of NVR by local ocular application of STO-609, a small molecule inhibitor of CaMKK2, in the aging model of NVR in experimental laser-induced CNV. Aged (16-month-old) mice underwent laser induction of CNV, were treated with daily periocular injection of either STO-609 (75 μg) or vehicle control, and underwent fluorescein angiography (FA) at day 14, prior to harvest of eyes for choroidal flatmount. By FA, STO-609 treated mice had smaller lesions with less leakage, as compared to vehicle control-treated mice. Additionally, STO-609 treated mice had predominantly capillary morphology with rare branching arterioles, diminished NVR as compared to vehicle control-treated mice. These data support the rationale that local ocular application of a pharmacologic inhibitor of CaMKK2 reduces NVR.

Our main approach is to develop STO-609 analogs with improved biophysical properties (i.e., selectivity, solubility, and potency) for future intravitreal formulation, by designing novel variants of the basic STO-609 scaffold. STO-609 is a planar molecule that fits into a narrow ATP binding pocket in CaMKK2. The crystal structure of compound-enzyme complex suggests three potential regions for modification (FIG. 8). We have designed structures in silico, and synthesized compounds for preliminary analysis. The most straightforward region to modify is the carboxylic acid moiety (FIG. 9). Novel amide derivatives have been designed and synthesized using this approach. Preliminary testing demonstrated greater solubility in relevant buffers.

6.2. In Vitro Screening Assay for Small Molecule Inhibitors of CaMKK2

Strategy and Methods: Utilizing a straightforward screening strategy, first assess the CaMKK2 inhibitory capacity of selected candidate molecules in cultured murine spleen-derived macrophages, to rank order relative potency of novel analogs, relative to STO-609. Briefly, cultured macrophages (derived from murine splenic monocytes, following generation of single-cell suspension from spleen and monocyte isolation and culture, by standard methods) will be activated by exposure to ionomycin (an activator of CaMKK2 activity) for 30 minutes. Cultured cells will be pretreated with varying concentrations of the molecules of interest for 1 hour prior to ionomycin exposure. Nonexposed cells will serve as a negative control. Following small molecule treatment, cells will be recovered and lysed for either 1) total protein or 2) mRNA. For total protein, Western blot densitometry analysis will be performed for phosphorylation of CaMKI, CaMKIV, and AMPK (substrates of CaMKK2), using this primary outcome to identify compounds with IC50<1 μM for at least one of these three target kinases, on three replicate assays. mRNA will be analyzed by qPCR, and secondary outcome will be demonstration of statistically significant reduction of mRNA content for at least one fibrogenic factor from among TGF-☐, CTGF, osteopontin, PDGF-BB, bFGF, IGF-1, using the IC50 concentration. However, all compounds meeting the target IC50 will be rank ordered by the % decrease in the mean of mRNA content for all six factors. For successful candidates, the same screening approach will be repeated in cultured human macrophage cell line, THP-1 cells, to affirm that selected candidate molecules are active in both human and murine macrophages. Parametric statistics will be used to compare metrics among groups of treated cells.

6.3. Compound Synthesis

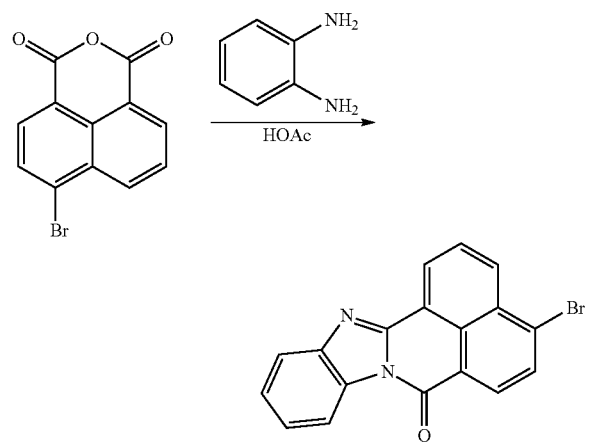

A mixture of 4-bromo-1,8-naphthoic anhydride (25 g, 90.2 mmol) and o-phenylenediamine (12 g, 110 mmol, 1.2 eq.) in 17M HOAc (500 mL) was heated to reflux for 4 h. After this time, the reflux condenser was replaced with a short-path vacuum distillation head and the reaction mixture was concentrated to near dryness under reduced pressure. The suspension was transferred to a 4L Erlenmeyer flask containing 1 L of ice water and a large magnetic stir bar. Solid NaHCO₃ (~300 g) was added in small portions with stirring and the bright yellow insoluble material was removed by vacuum filtration. The filter cake was washed with saturated aqueous NaHCO₃ (1L), H₂O (1 L) and dried in vacuo over the weekend giving the pure product as a bright yellow powder (31.2 g, 99%). ESIMS: m/z=349 [(M+H)⁺].

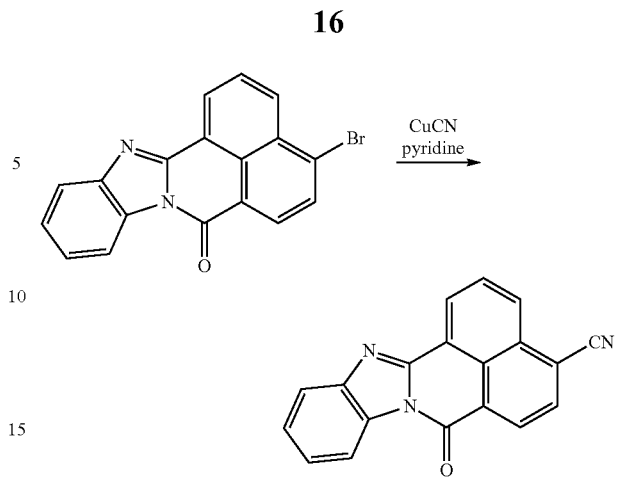

The bromide (21 g, 60 mmol) was added portion wise to pyridine (250 mL) in a 500 mL thick walled pressure vessel with stirring (if you add solvent directly to the dry powder at this scale or just add the bromide in one portion to the stirring solvent, the mixture will not stir effectively) Copper (I) cyanide (9.2 g, 102 mmol, 1.7 eq.) was then added in one portion and the mixture was heated in a heavy walled pressure vessel (150 ° C., bath temperature) for 25h. The mixture was cooled to room temperature then poured into concentrated NH₄OH (1000 mL)/ice (1000 mL). The resulting suspension was stirred until the ice melted. Insolubles were removed by vacuum filtration and the muddy brown filter cake was washed with H₂O (1000 mL), 1N HCl (1000 mL), H₂O (1000 mL), then dried in vacuo giving the crude product as a brown powder (22 g). ESIMS: m/z=296 [(M+H)⁺].

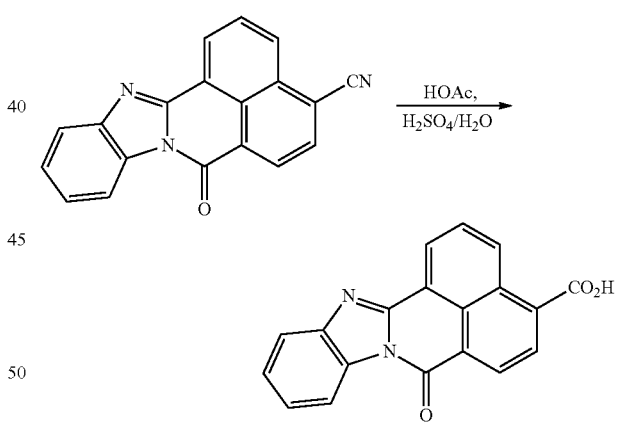

A mixture of the crude nitrile (21.1 g, 71 mmol), 17M HOAc (200 mL), 18M H₂SO₄ (80 mL) and H₂O (60 mL) were heated to reflux for 24 h after which time analysis of the reaction mixture by TLC (25% EtOAc in hexanes) indicated essentially complete consumption of starting nitrile. The reaction mixture was cooled to room temperature and the mixture was diluted with ice H₂O (1 L). The resulting brown suspension was stirred for 2h and was then subjected to cetrifugation (2500 rpm, 5 min.). The supernatant was removed by decantation. The precipitate was washed with H₂O (2×500 mL), and dried overnight in vacuo. The following morning the black-brown filter cake was suspended in 1N NaOH (3 L). The resulting suspension was stirred at room temperature for 5 h then filtered at the vacuum. The filtrate was extracted with MTBE (6×2 L) then carefully acidified (pH 3-4) with 17 M HOAc. Insolubles were removed by filtration and dried in vacuo overnight. The resulting solid was suspended in MeOH (1 L) and filtered. The filtrate was concentrated to dryness under reduced pressure giving the product as a yellow-orange solid (15 g, 58%). ESIMS: m/z=315 [(M+H)+]

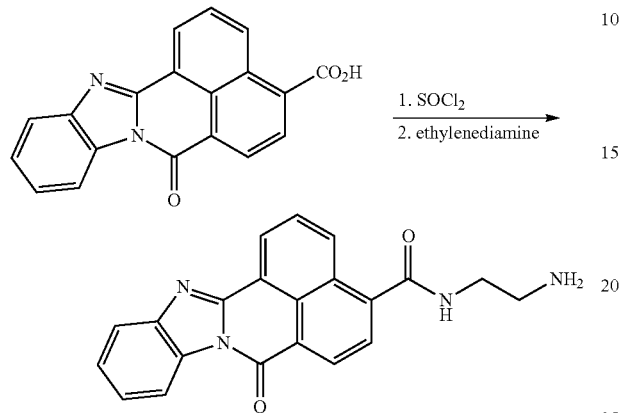

Thionyl chloride (5 mL) was added to STO-609 (100 mg) and the heterogeneous mixture was heated to reflux for 2h after which time the reaction mixture became homogeneous. After cooling to room temperature, volatiles were removed under reduced pressure giving the crude acid chloride as a reddish solid. The solid was suspended in anhydrous CH$_2$Cl$_2$ (5 mL) and the resulting suspension was added dropwise over 2-3 minutes to an ice-NaCl bath cooled solution of ethylenediamine (1 mL) in CH$_2$Cl$_2$ (10 mL). The reaction mixture was allowed to warm to room temperature as the cooling bath melted. Stirring was continued overnight and the reaction mixture was poured into ice cold brine (25 mL). The resulting suspension was filtered (fine frit) and the filtrate was extracted with EtOAc (5×50 mL). The combined extracts were dried (MgSO$_4$). The drying agent was removed by filtration and the filtrate was concentrated to dryness under reduced pressure giving the pure amide as a dark orange powder (35.2 mg, 37%). ESIMS: m/z=357 [(M+H)$^x$].

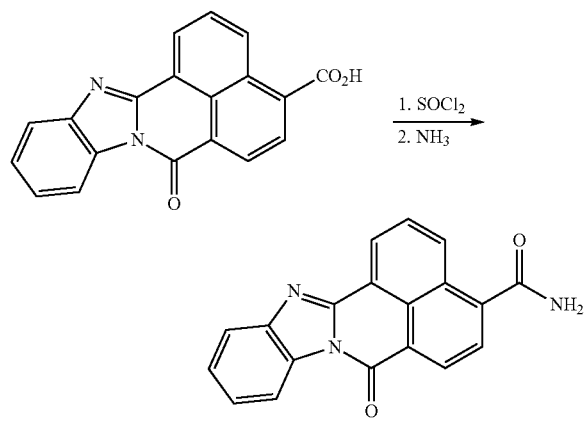

Thionyl chloride (5 mL) was added to STO-609 (100 mg) and the heterogeneous mixture was heated to reflux for 2 h after which time the reaction mixture became homogeneous. After cooling to room temperature, volatiles were removed under reduced pressure giving the crude acid chloride as a reddish solid. The solid was dissolved in anhydrous CH$_2$Cl$_2$ (50 mL) and the resulting very slight suspension was filtered (fine frit Buchner funnel). The filtrate was cooled in a dry ice/acetone bath and NH$_3$ added dropwise over 2-3 minutes to an ice-NaCl bath cooled solution of ethylenediamine (1 mL) in CH$_2$Cl$_2$ (10 mL). The reaction mixture was allowed to warm to room temperature as the cooling bath melted. Stirring was continued overnight and the reaction mixture was poured into ice cold brine (25 mL). The resulting suspension was filtered (fine frit) and the filtrate was extracted with EtOAc (5×50 mL). The combined extracts were dried (MgSO$_4$). The drying agent was removed by filtration and the filtrate was concentrated to dryness under reduced pressure giving the pure amide as a dark orange powder (42 mg, 43%). ESIMS: m/z=314 [(M+H)+].

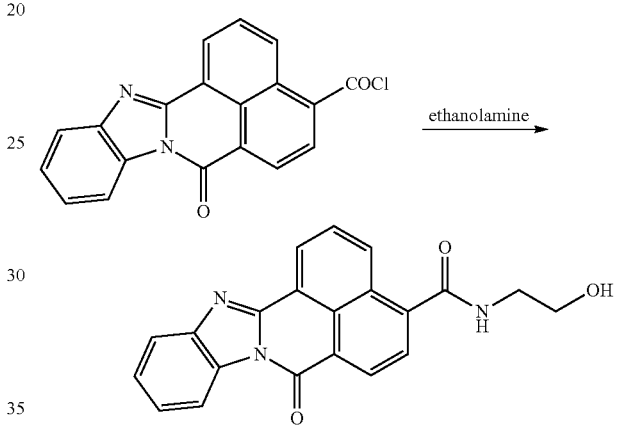

The acid chloride (100 mg, 0.3 mmol) solid was suspended in anhydrous CH$_2$Cl$_2$ (5 mL) and the resulting suspension was added dropwise over 2-3 minutes to a dry ice/isopropyl alcohol bath cooled solution of ethanolamine (2 mL) in CH$_2$Cl$_2$ (10 mL). The reaction mixture was allowed to warm to room temperature as the cooling bath melted. Stirring was continued overnight and the reaction mixture was concentrated to near dryness under reduced pressure. The resulting thick residue was treated with brine (50 mL). The mixture was stirred for 5 minutes then filtered (fine frit). The filtrate was extracted with EtOAc (5×50 mL). The combined extracts were dried (MgSO$_4$). The drying agent was removed by filtration and the filtrate was concentrated to dryness under reduced pressure giving the pure (by LCMS) amide as a dark orange powder (38 mg, 35%). ESIMS: m/z=358 [(M+H)+].

7. REFERENCES

1. Espinosa-Heidmann D G, Suner I J, Hernandez E P, Monroy D, Csaky K G, Cousins S W. Macrophage depletion diminishes lesion size and severity in experimental choroidal neovascularization. Investigative ophthalmology & visual science. 2003; 44(8): 3586-92. Epub 2003 Jul. 29. PubMed PMID: 12882811.
2. Sakurai E, Anand A, Ambati B K, van Rooijen N, Ambati J. Macrophage depletion inhibits experimental choroidal neovascularization. Investigative ophthalmology & visual science. 2003; 44(8): 3578-85. Epub 2003 Jul. 29. PubMed PMID: 12882810.

3. Zhao H, Roychoudhury J, Doggett T A, Apte RS, Ferguson T A. Age-dependent changes in FasL (CD95L) modulate macrophage function in a model of age-related macular degeneration. Investigative ophthalmology & visual science. 2013; 54(8): 5321-31. Epub 2013 Jul. 04. doi: 10.1167/iovs.13-12122. PubMed PMID: 23821188; PubMed Central PMCID: PMC3738220.
4. Sene A, Khan A A, Cox D, Nakamura R E, Santeford A, Kim B M, et al. Impaired cholesterol efflux in senescent macrophages promotes age-related macular degeneration. Cell metabolism. 2013; 17(4): 549-61. Epub 2013 Apr. 09. doi: 10.1016/j.cmet.2013.03.009. PubMed PMID: 23562078; PubMed Central PMCID: PMC3640261.
5. Raoul W, Auvynet C, Camelo S, Guillonneau X, Feumi C, Combadiere C, et al. CCL2/CCR2 and CX3CL1/CX3CR1 chemokine axes and their possible involvement in age-related macular degeneration. Journal of neuroinflammation. 2010;7:87. Epub 2010 Dec. 04. doi: 10.1186/1742-2094-7-87. PubMed PMID: 21126357; PubMed Central PMCID: PMC3003653.
6. Frigo D E, Howe M K, Wittmann B M, Brunner A M, Cushman I, Wang Q, et al. CaM kinase kinase beta-mediated activation of the growth regulatory kinase AMPK is required for androgen-dependent migration of prostate cancer cells. Cancer research. 2011; 71(2): 528-37. Epub 2010 Nov. 26. doi: 10.1158/0008-5472.CAN-10-2581. PubMed PMID: 21098087; PubMed Central PMCID: PMC3074523.
7. Racioppi L, Noeldner P K, Lin F, Arvai S, Means A R. Calcium/calmodulin-dependent protein kinase kinase2 regulates macrophage-mediated inflammatory responses. The Journal of biological chemistry. 2012; 287(14): 11579-91. Epub 2012 Feb. 16. doi: 10.1074/jbc.M111.336032. PubMed PMID: 22334678; PubMed-Central PMCID: PMC3322820.
8. Mcdonnell D P, Frigo D, Means A R. Camkk-beta as a target for treating cancer. Google Patents; 2013.
9. McDonnell D P. CaMKK2: A Druggable Target that Regulates Macrophage Function in Breast Cancer ww3.komen.org/Flashviewer/Grants_Table/FY13/2013researchgrantspdf/IIR13264868.pdf: Susan G. Komen Foundation; 2013 [cited 2015 Aug. 1].
10. Monteiro P, Gilot D, Langouet S, Fardel O. Activation of the aryl hydrocarbon receptor by the calcium/calmodulin-dependent protein kinase kinase inhibitor 7-oxo-7H-benzimidazo[2,1-a]benz[de]isoquinoline-3-carboxylic acid (STO-609). Drug metabolism and disposition: the biological fate of chemicals. 2008; 36(12): 2556-63. Epub 2008 Aug. 30. doi: 10.1124/dmd.108.023333. PubMed PMID: 18755850.
11. Raghava S, Hammond M, Kompella U B. Periocular routes for retinal drug delivery. Expert opinion on drug delivery. 2004; 1(1): 99-114. Epub 2005 Nov. 22. doi: 10.1517/17425247.1.1.99. PubMed PMID: 16296723.
12. Brown D M, Kaiser P K, Michels M, Soubrane G, Heier J S, Kim R Y, et al. Ranibizumab versus verteporfin for neovascular age-related macular degeneration. The New England journal of medicine. 2006; 355(14): 1432-44. Epub 2006 Oct. 06. doi: 10.1056/NEJMoa062655. PubMed PMID: 17021319.
13. Rosenfeld P J, Brown D M, Heier J S, Boyer D S, Kaiser P K, Chung C Y, et al. Ranibizumab for neovascular age-related macular degeneration. The New England journal of medicine. 2006; 355(14): 1419-31. Epub 2006 Oct. 06. doi: 10.1056/NEJMoa054481. PubMed PMID: 17021318.
14. Heier J S, Brown D M, Chong V, Korobelnik J F, Kaiser P K, Nguyen Q D, et al. Intravitreal Aflibercept (VEGF Trap-Eye) in Wet Age-related Macular Degeneration. Ophthalmology. 2012. Epub 2012 Oct. 23. doi: 10.1016/j.ophtha.2012.09.006. PubMed PMID: 23084240.
15. Congdon N, O'Colmain B, Klaver C C, Klein R, Munoz B, Friedman D S, et al. Causes and prevalence of visual impairment among adults in the United States. Archives of ophthalmology. 2004; 122(4): 477-85. Epub 2004 Apr. 14. doi: 10.1001/archopht.122.4.477. PubMed PMID: 15078664.
16. Green W R. Histopathology of age-related macular degeneration. Mol Vis. 1999; 5: 27. Epub 1999 Nov. 17. PubMed PMID: 10562651.
17. Martin D F, Maguire M G, Fine S L, Ying G S, Jaffe G J, Grunwald J E, et al. Ranibizumab and bevacizumab for treatment of neovascular age-related macular degeneration: two-year results. Ophthalmology. 2012; 119(7): 1388-98. Epub 2012 May 05. doi: 10.1016/j.ophtha.2012.03.053. PubMed PMID: 22555112; PubMed Central PMCID: PMC3389193.
18. Martin D F, Maguire M G, Ying G S, Grunwald J E, Fine S L, Jaffe G J. Ranibizumab and bevacizumab for neovascular age-related macular degeneration. The New England journal of medicine. 2011; 364(20) 1897-908. Epub 2011 Apr. 30. doi: 10.1056/NEJMoa1102673. PubMed PMID: 21526923; PubMed Central PMCID: PMC3157322.
19. Rosenfeld P J, Shapiro H, Tuomi L, Webster M, Elledge J, Blodi B. Characteristics of patients losing vision after 2 years of monthly dosing in the phase III ranibizumab clinical trials. Ophthalmology. 2011; 118(3): 523-30. Epub 2010 Oct. 06. doi: 10.1016/j.ophtha.2010.07.011. PubMed PMID: 20920825.
20. Ying G S, Kim B J, Maguire M G, Huang J, Daniel E, Jaffe G J, et al. Sustained Visual Acuity Loss in the Comparison of Age-Related Macular Degeneration Treatments Trials. JAMA ophthalmology. 2014. Epub 2014 May 31. doi: 10.1001/jamaophthalmol.2014.1019. PubMed PMID: 24875610.
21. Mettu P S, Crowell S, Shaw J, Grunwald L, Lad E M, Serrano N, et al. Neovascular Morphology on ICG Angiography Predicts Response to Anti-VEGF Therapy in Eyes with Serous Pigment Epithelial Detachments and Age-Related Macular Degeneration. Invest Ophthalmol Vis Sci. 2012; 53(6): 2654.
22. Serrano N P, Shaw J, Mettu P S, Lad EM, Crowell S, Cousins S W. High-speed Indocyanine Green Angiography In Age Related Macular Degeneration With Fibrovascular Pigment Epithelial Detachments. Invest Ophthalmol Vis Sci. 2012; 53(6): 1151.
23. Lad E M, Grunwald L, Mettu P S, Serrano N P, Crowell S, Cousins S W. Lesion Morphology on Indocyanine Green Angiography in Age-Related Macular Degeneration with Classic Choroidal Neovascular Membrane: Implications for Response to anti-VEGF Treatment. Invest Ophthalmol Vis Sci. 2012; 53(6): 5161.
24. Espinosa-Heidmann D G, Suner I, Hernandez E P, Frazier W D, Csaky K G, Cousins S W. Age as an independent risk factor for severity of experimental choroidal neovascularization. Invest Ophthalmol Vis Sci. 2002; 43(5): 1567-73. Epub 2002 May 01. PubMed PMID: 11980875.
25. Mettu P S, Saloupis P, Cousins S W. PAMP Stimulation of Macrophages Promotes Neovascular Remodeling in Experimental Choroidal Neovascularization. Invest Ophthalmol Vis Sci. 2014; 55(5): 1198.

26. Suner I J, Espinosa-Heidmann D G, Pereira-Simon S, Pina Y, Cousins S W. Cigarette Smoke Increases Severity of Experimental Choroidal Neovascularization (CNV): Role of Inflammation. Invest Ophthalmol Vis Sci. 2005; 46(5): 3507.
27. Lad E M, Hammill B G, Qualls L G, Wang F, Cousins S W, Curtis L H. Anti-VEGF treatment patterns for neovascular age-related macular degeneration among medicare beneficiaries. American journal of ophthalmology. 2014; 158(3): 537-43 e2. Epub 2014 May 27. doi: 10.1016/j.ajo.2014.05.014. PubMed PMID: 24857687.
28. Curtis L H, Hammill B G, Qualls L G, DiMartino L D, Wang F, Schulman K A, et al. Treatment patterns for neovascular age-related macular degeneration: analysis of 284 380 medicare beneficiaries. American journal of ophthalmology. 2012; 153(6): 1116-24 el. Epub 2012 Feb. 11. doi: 10.1016/j.ajo.2011.11.032. PubMed PMID: 22321802.
29. Espinosa-Heidmann D G, Malek G, Mettu P S, Caicedo A, Saloupis P, Gach S, et al. Bone marrow transplantation transfers age-related susceptibility to neovascular remodeling in murine laser-induced choroidal neovascularization. Invest Ophthalmol Vis Sci. 2013; 54(12): 7439-49. Epub 2013 Oct. 19. doi: 10.1167/iovs.13-12546. PubMed PMID: 24135751; PubMed Central PMCID: PMC3828044.
30. Tatar O, Shinoda K, Kaiserling E, Claes C, Eckardt C, Eckert T, et al. Implications of bevacizumab on vascular endothelial growth factor and endostatin in human choroidal neovascularisation. The British journal of ophthalmology. 2009; 93(2): 159-65. Epub 2008 Oct. 08. doi: 10.1136/bjo.2008.138594. PubMed PMID: 18838410.
31. Racioppi L, Means A R. Calcium/calmodulin-dependent protein kinase kinase 2: roles in signaling and pathophysiology. The Journal of biological chemistry. 2012; 287 (38): 31658-65. Epub 2012 Jul. 11. doi: 10.1074/jbc.R112.356485. PubMed PMID: 22778263; PubMed Central PMCID: PMC3442500.
32. Racioppi L. CaMKK2: a novel target for shaping the androgen-regulated tumor ecosystem. Trends in molecular medicine. 2013; 19(2): 83-8. Epub 2013 Jan. 22. doi: 10.1016/j.molmed.2012.12.004. PubMed PMID: 23332598; PubMed Central PMCID: PMC3565098.
33. Tokumitsu H, Inuzuka H, Ishikawa Y, Ikeda M, Saji I, Kobayashi R. STO-609, a specific inhibitor of the Ca(2+)/calmodulin-dependent protein kinase kinase. The Journal of biological chemistry. 2002; 277(18): 15813-8. Epub 2002 Feb. 28. doi: 10.1074/jbc.M201075200. PubMed PMID: 11867640.
34. Tokumitsu H, Inuzuka H, Ishikawa Y, Kobayashi R. A single amino acid difference between alpha and beta Ca2+/calmodulin-dependent protein kinase kinase dictates sensitivity to the specific inhibitor, STO-609. The Journal of biological chemistry. 2003; 278(13): 10908-13. Epub 2003 Jan. 24. doi: 10.1074/jbc.M213183200. PubMed PMID: 12540834.
35. Teng E C, Racioppi L, Means A R. A cell-intrinsic role for CaMKK2 in granulocyte lineage commitment and differentiation. Journal of leukocyte biology. 2011; 90(5): 897-909. Epub 2011 Aug. 06. doi: 10.1189/jlb.0311152. PubMed PMID: 21816924; PubMed Central PMCID: PMC3206468.
36. Schlereth S, Lee H S, Khandelwal P, Saban D R. Blocking CCR7 at the ocular surface impairs the pathogenic contribution of dendritic cells in allergic conjunctivitis. The American journal of pathology. 2012; 180(6): 2351-60. Epub 2012 Apr. 18. doi: 10.1016/j.ajpath.2012.02.015. PubMed PMID: 22507838.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A method of modulating CaMKK2 in a subject comprising administering to the subject an effective amount of a compound comprising the Formula (I):

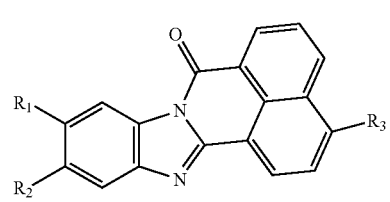

Formula (I)

or a pharmaceutically acceptable salt, solvate, hydrate, or derivative thereof, wherein $R_1$ and $R_2$ are Hydrogen (H), and $R_3$ is selected from the group consisting of

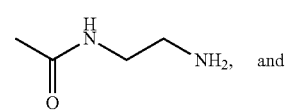

formula (II)

and

-continued formula (III)

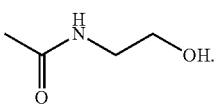

2. A method of inhibiting CaMKK2 in a subject comprising administering to the subject an effective amount of a compound comprising the Formula (I):

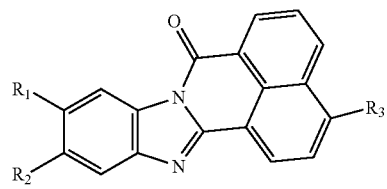

Formula (I)

or a pharmaceutically acceptable salt, solvate, hydrate, or derivative thereof, wherein $R_1$ and $R_2$ are Hydrogen (H), and $R_3$ is selected from the group consisting of

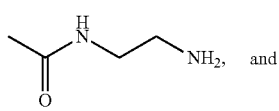

formula (II)

and formula (III)

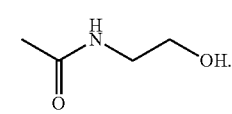

formula (III)

3. A method of modulating CaMKK2 in a subject comprising administering to the subject an effective amount of a compound comprising the Formula (I)

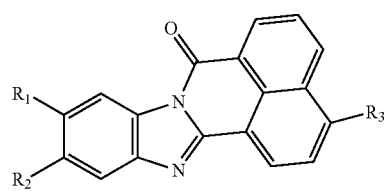

Formula (I)

or a pharmaceutically acceptable salt, solvate, hydrate, or derivative thereof, wherein $R_3$ is Carboxylic acid ($CO_2H$), and both $R_1$ and $R_2$ are selected from the group:

formula (VI)

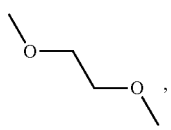

formula (VI)

formula (VII)

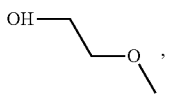

formula (VII)

formula (VIII)

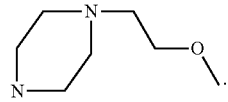

formula (VIII)

4. The method of claim 1, wherein the compound comprises the chemical formula:

Formula (XI)

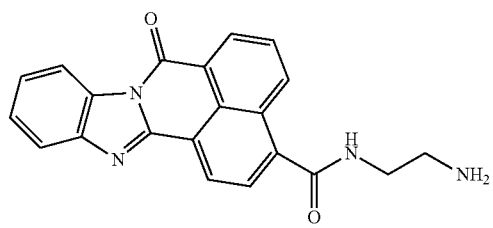

or a pharmaceutically acceptable salt, solvate, hydrate, or derivative thereof.

5. The method of claim 1, wherein the compound comprises the chemical formula:

Formula (X)

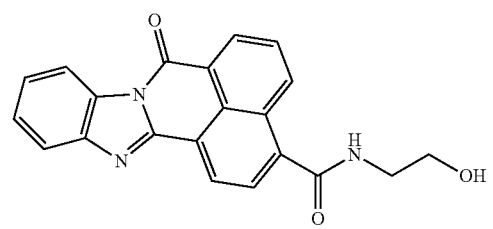

or a pharmaceutically acceptable salt, solvate, hydrate, or derivative thereof.

6. The method of claim 3, wherein the compound comprises the chemical formula:

Formula (XIII)

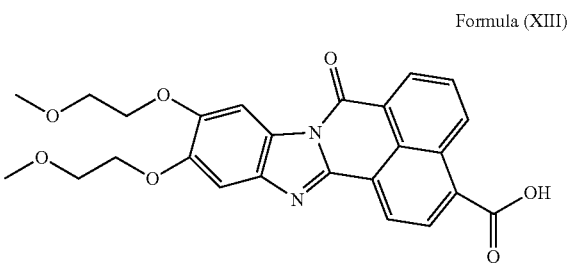 [SMILES: COCCOc1cc2nc3c4ccc(C(=O)O)c5cccc(c(=O)n3c2cc1OCCOC)c54]

or a pharmaceutically acceptable salt, solvate, hydrate, or derivative thereof.

7. The method of claim 3, wherein the compound comprises the chemical formula:

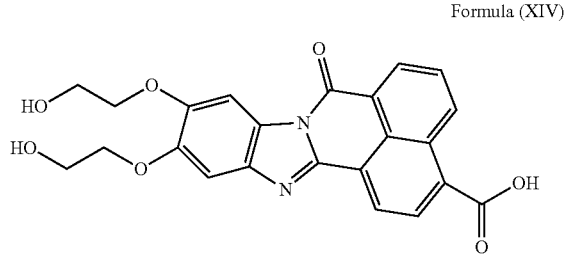 [SMILES: O=C(O)c1ccc2c3c1cccc3c(=O)n1c3cc(OCCO)c(OCCO)cc3nc21]

Formula (XIV)

or a pharmaceutically acceptable salt, solvate, hydrate, or derivative thereof.

8. The method of claim 3, wherein the compound comprises the chemical formula:

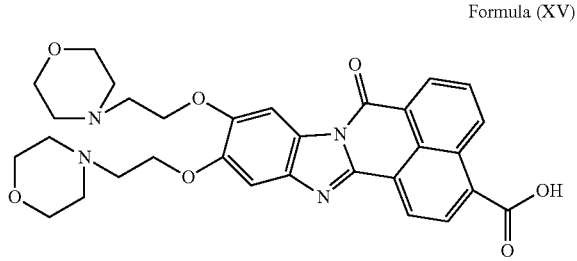 [SMILES: O=C(O)c1ccc2c3c1cccc3c(=O)n1c3cc(OCCN4CCOCC4)c(OCCN4CCOCC4)cc3nc21]

Formula (XV)

or a pharmaceutically acceptable salt, solvate, hydrate, or derivative thereof.

9. A method of inhibiting CaMKK2 in a subject comprising administering to the subject an effective amount of a compound comprising the Formula (I)

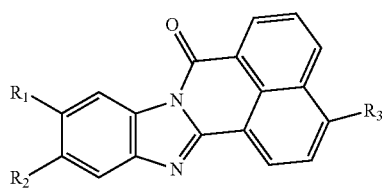

Formula (I)

or a pharmaceutically acceptable salt, solvate, hydrate, or derivative thereof, wherein $R_3$ is Carboxylic acid ($CO_2H$), and both $R_1$ and $R_2$ are selected from the group:

formula (VI)

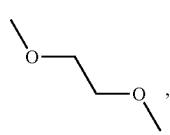

formula (VII)

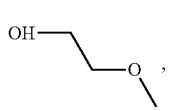

formula (VIII)

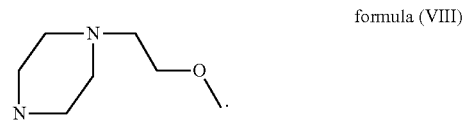

10. The method of claim 2, wherein the compound comprises the chemical formula:

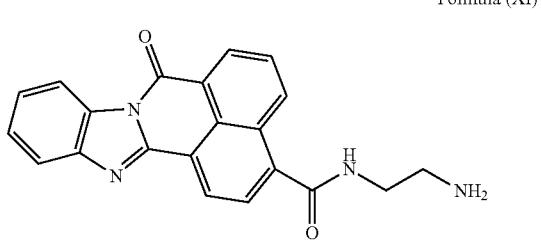

Formula (XI)

or a pharmaceutically acceptable salt, solvate, hydrate, or derivative thereof.

11. The method of claim 2, wherein the compound comprises the chemical formula:

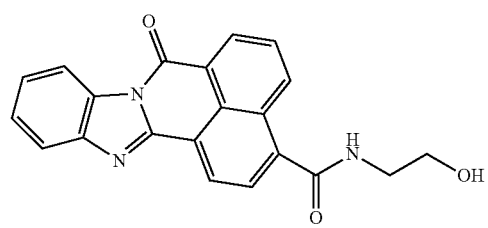

Formula (X)

or a pharmaceutically acceptable salt, solvate, hydrate, or derivative thereof.

12. The method of claim 9, wherein the compound comprises the chemical formula:

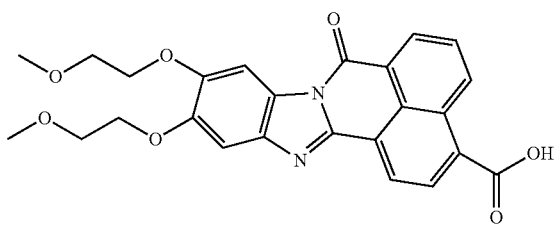

Formula (XIII)

or a pharmaceutically acceptable salt, solvate, hydrate, or derivative thereof.

13. The method of claim 9, wherein the compound comprises the chemical formula:

Formula (XIV)
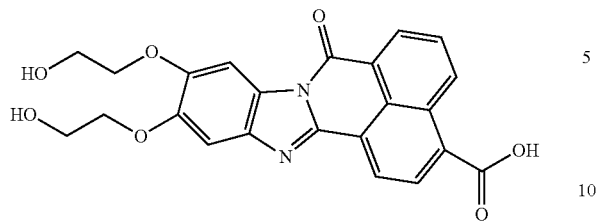
or a pharmaceutically acceptable salt, solvate, hydrate, or derivative thereof.
14. The method of claim 9, wherein the compound comprises the chemical formula:
Formula (XV)
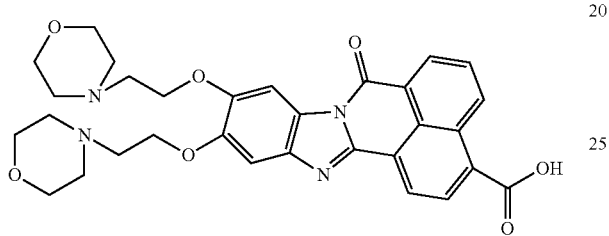
or a pharmaceutically acceptable salt, solvate, hydrate, or derivative thereof.
* * * * *